(12) United States Patent
Drynkin et al.

(10) Patent No.: US 9,365,373 B1
(45) Date of Patent: Jun. 14, 2016

(54) LABORATORY TUBE CAP PRESENTER FOR CAPPING LABORATORY TUBES

(71) Applicants: Alexander V. Drynkin, San Ramon, CA (US); David B. Miller, Orinda, CA (US)

(72) Inventors: Alexander V. Drynkin, San Ramon, CA (US); David B. Miller, Orinda, CA (US)

( * ) Notice: Subject to any disclaimer, the term of this patent is extended or adjusted under 35 U.S.C. 154(b) by 222 days.

(21) Appl. No.: 13/815,386

(22) Filed: Feb. 26, 2013

Related U.S. Application Data

(60) Provisional application No. 61/742,400, filed on Aug. 10, 2012.

(51) Int. Cl.
*B65H 3/02* (2006.01)

(52) U.S. Cl.
CPC ....................................... *B65H 3/02* (2013.01)

(58) Field of Classification Search
USPC ......... 221/159, 210, 213, 224, 233, 235, 239, 221/254, 255, 259
See application file for complete search history.

(56) References Cited

U.S. PATENT DOCUMENTS

| 2,586,281 | A | * | 2/1952 | Wilson | 53/67 |
| 2,916,125 | A | * | 12/1959 | Wallberg | 193/40 |
| 3,410,452 | A | * | 11/1968 | Igel et al. | 221/13 |
| 4,828,142 | A | * | 5/1989 | McKnight | 221/171 |
| 6,497,083 | B1 | * | 12/2002 | Garwood et al. | 53/244 |

* cited by examiner

*Primary Examiner* — Gene Crawford
*Assistant Examiner* — Kelvin L Randall, Jr.
(74) *Attorney, Agent, or Firm* — Richard Esty Peterson (57) ABSTRACT

A laboratory tube cap presenter for a tube, such as a test tube, a medical vial or other vessel that may be capped by an automated capper in a robotic tube handling apparatus, the tube cap presenter having a magazine of pre-oriented tube caps that cooperates with a selector mechanism and a shuttle mechanism to transport a selected tube cap to a presentation station where the tube cap is oriented for pick up by the pickup mechanism of a robotic tube handling apparatus.

18 Claims, 7 Drawing Sheets

LABORATORY TUBE CAP PRESENTER FOR CAPPING LABORATORY TUBES

CROSS-REFERENCE TO RELATED APPLICATIONS

The present invention is based on U.S. Provisional Patent Application Ser. No. 61/742,400, filed Aug. 10, 2012 entitled, "Laboratory Tube Cap Presenter for Capping Laboratory Tubes," filed in the names of Alexander V. Drynkin and David B. Miller. The priority of this provisional application is hereby claimed and the application is hereby incorporated herein by reference thereto.

BACKGROUND OF THE INVENTION

This invention relates to a laboratory tube cap presenter in the form of a machine that automates the task of orienting and positioning the cap of a laboratory tube, typically a test or sample tube that is processed by an automated or robotic tube handler. A tube handler moves one or more laboratory tubes from station to station for any of a variety of laboratory procedures. Frequently, the laboratory tube is capped at some step in the procedure necessitating the cap to be positioned at a pickup location before capping.

There exist tube cap feeders that position and orient tube caps for pickup by an automatic tube handler. However, the task of feeding tube caps from a supply to a robotic tube handling apparatus becomes substantially more difficult when the height of the tube cap is less than its diameter. For such a condition, the feed process is challenging because the tube cap can easily become disoriented when in a stacked column. The disoriented tube cap can then jam the feed mechanism, halting the automated tube handling process.

The laboratory tube cap presenter of this invention is designed to feed tube caps, including the difficult to handle cap that has a height that is less than the diameter of the cap, to a location and in an orientation to be transferred to a capping station. The tube cap is then typically transported to a capping station by automated tube handling apparatus where the tube cap is installed on a laboratory tube by a capping mechanism.

SUMMARY OF THE INVENTION

The laboratory tube cap presenter of this invention is designed to individually feed tube caps from a bulk supply of laboratory tube caps to a location and in an orientation that can be transferred to a capping station. The laboratory tube cap presenter is particularly designed to co-operate with a robotic tube handling apparatus having a picker mechanism that engages the presented cap and transports the cap to a capping station. The laboratory tube cap presenter in its preferred embodiment is constructed to engage a magazine or cartridge of pre-oriented tube caps and shuttle selected caps to the presentation station where the cap can automatically or manually be retrieved for further processing. Typically the automated tube cap presenter is an auxiliary component in an automated tube capping operation and cooperates with a robotic tube handler.

DETAILED DESCRIPTION OF THE PREFERRED EMBODIMENT

Figure 1:
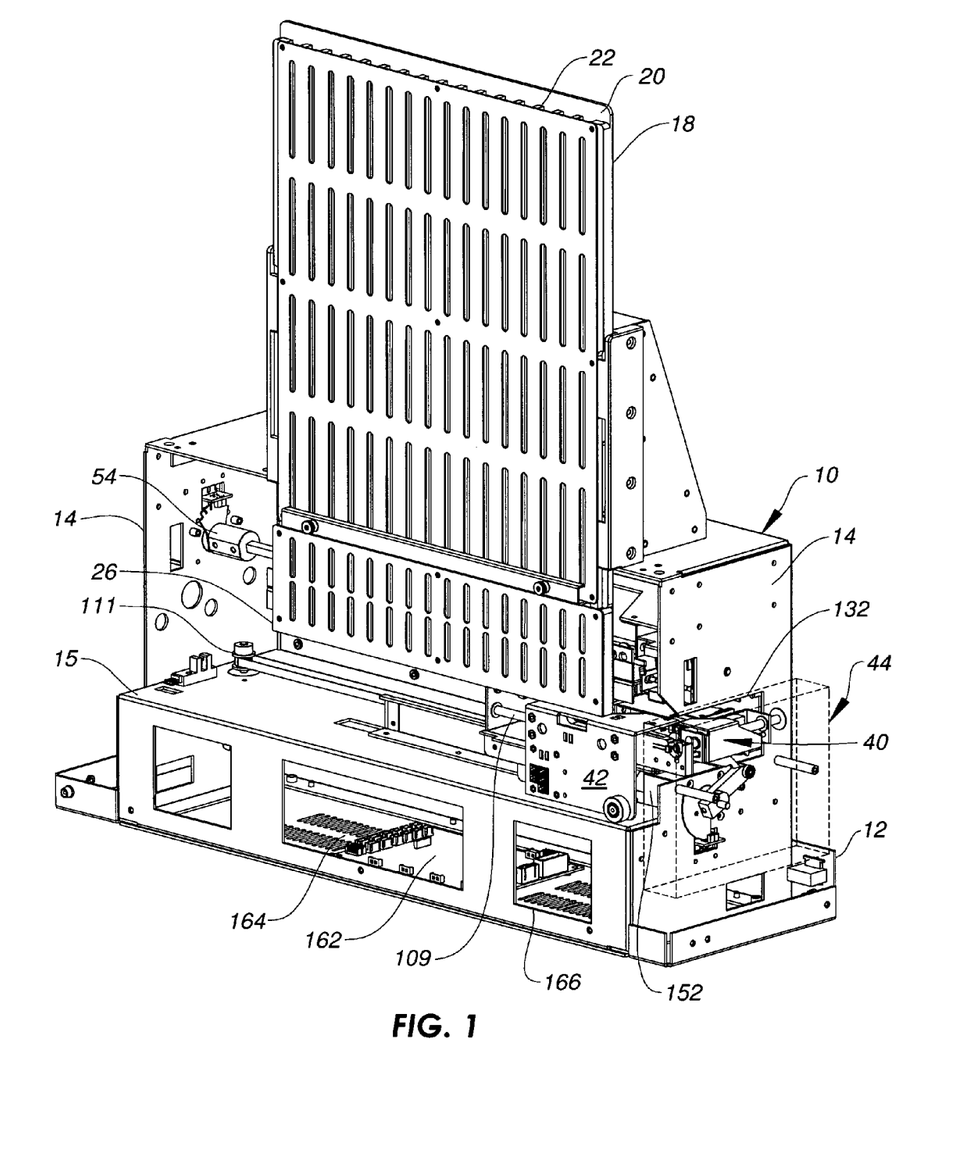
FIG. 1 is a perspective view of the laboratory tube cap presenter of this invention with an outer casing removed to reveal the operational components.
Figure 2:
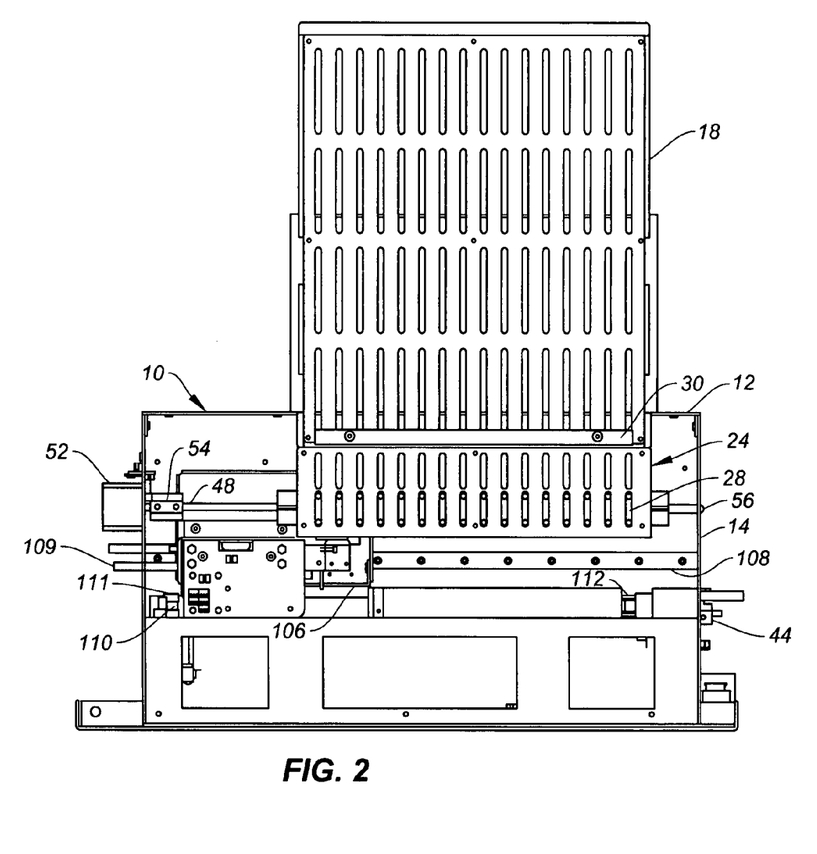
FIG. 2 is a front elevational view of the tube cap presenter of FIG. 1 with a tube cap carrier in an alternate position.

The laboratory tube cap presenter of this invention, shown in FIGS. 1 and 2, is designated generally by the reference numeral 10. The construction of the tube cap presenter 10 is designed as a desk top component that typically co-operates with a robotic tube handling apparatus having a picker mechanism that can retrieve a tube cap presented for pickup by the subject tube cap presenter. It is to be understood that the presented tube cap can be manually retrieved or retrieved by any of a variety of different mechanical mechanisms. As such, modifications to the component construction to accommodate different systems for which the tube cap presenter 10 is an accessory are to be expected and do not affect the core invention disclosed herein as a preferred embodiment and are therefore not shown herein.

Figure 3:
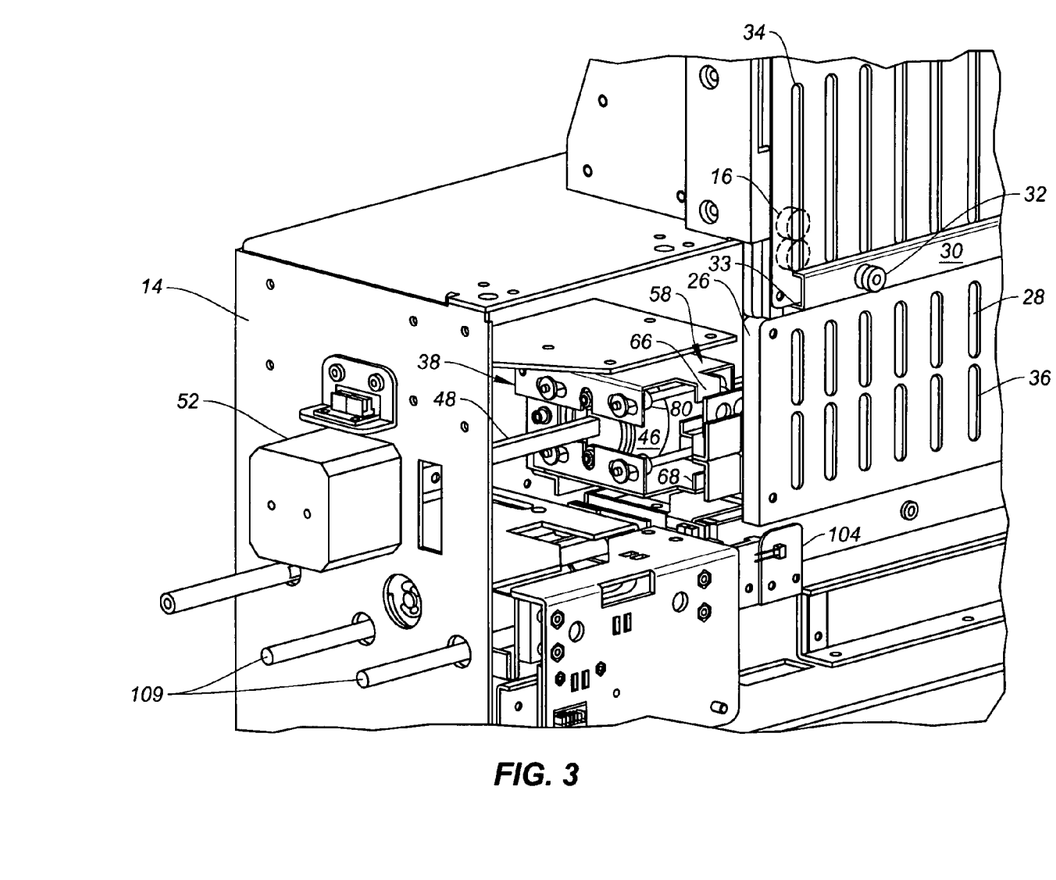
FIG. 3 is an enlarged partial perspective view of a portion of the tube cap presenter of FIG. 2 with the tube cap carrier in the alternate position.

As shown in FIGS. 1 to 3, the tube cap presenter 10 has an external housing 12 that is in part removed to reveal the internal sheet-metal frame 14 with an intermediate deck 15 for containing and supporting the electro-mechanical assemblies for extracting a tube cap 16 from a storage magazine 18. The storage magazine 18 holds hundreds of tube caps 16 in vertical guide channels 20 formed by dividers 22. In the storage magazine 18 the tube caps 16, typically flat tube caps, are oriented side-to-side with the axis of the circular caps being horizontal rather that the traditional stacking of tube caps on a vertical axis in a cylindrical column. In stacking the tube caps 16 in a channel, the flat tube caps, which typically have a height less that the cap diameter, do not become disoriented and jammed in the magazine 18 during depletion. The storage magazine 18 is preferably detachable for quick replacement with a filled magazine or substitution with a magazine of different caps in size, color or configuration.

The storage magazine 18 abuts a sorting shunt 24 that has a gateway panel 26 with similar guide channels 28 that are aligned with the guide channels 20 of the magazine 18 as shown in the enlarged partial perspective view of FIG. 3. It is contemplated that the storage magazine 18 is replaceable in the manner of a pre-loaded cartridge and therefore each magazine includes a barrier blade 30 with a blade stop 33 that locates at the bottom of the magazine to prevent the caps from escaping during installation or replacement. The two protruding thumbscrews 32 allow easy removal of the barrier blade 30 before operation. The storage magazine 18 and the gateway panel 26 of the sorting shunt 24 have open slots 34 and 36 along the major portion of the guide channels 20 and 28 to allow visual inspection of the content of the magazine 18 and gateway panel 26. These slots 34 and 36 may permit limited corrective action in the rare event of a feed problem because of a disoriented cap.

The sorting shunt 24 includes a displaceable actuator assembly 40 that includes a block and release mechanism 38 and a cap carrier 42 for transport of a released cap 16 to an orientation station 44. The displaceable block and release mechanism 38 has a spool 46 that slides on a square spindle 48 connected at one distal end 50 to the shaft (not shown) of a drive motor 52 by a collet 54 and at the other end to a bearing 56 mounted to the internal frame 14. Incremental rotation of the spindle 48 on electrical command, rotates the spool 46. The spool 46 is rotated about twenty degrees in opposite directions from a home position by the drive motor 52 for generating the reversible linear motion in the block and release mechanism 38.

Figure 4:
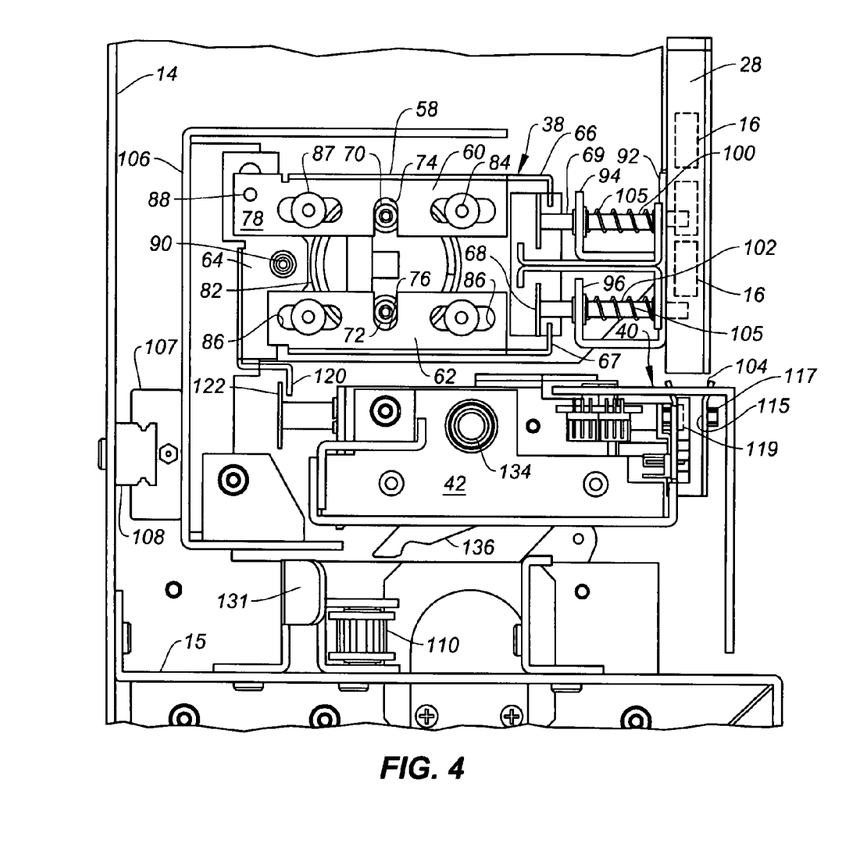
FIG. 4 is an enlarged partial cross-sectional view of the apparatus of FIG. 3.

The spool 46 of the block and release mechanism 38 has a structural cage 58 shown also in FIG. 4 with upper and lower slotted channel members 60 and 62 that bracket the spool 46 and connect to a pivotal back plate 64. The construction as shown in FIGS. 3 and 4 allows reverse linear reciprocal motion of two hooked fingers 66 and 67 extending from the channel members 60 and 62, respectively. The hooked fingers 66 and 67 engage the flange 68 of selected blocking pins 69.

This restricted movement in the block and release mechanism 38 is accomplished by bearing pins 70 and 72 projecting from each end of the spool 46 that engage open slots 74 and 76 in the side elements 78 of the channel members 60 and 62. The open slots 74 and 76 accommodate the slight vertical displacement of the bearing pins 70 and 72 on partial rotation of the spool 46. Horizontal displacement of the slotted channel members 60 and 62 without corresponding vertical displacement is accomplished by guide rollers 80 that ride on the spool surface 82 and have extending shafts 84 that extend into elongated slots 86 in the side elements 78 of the channel members 60 and 62. The shafts 84 are positioned and retained by clips 87. The pivotal interconnection of the channel members 60 and 62 with the back plate 64 by pin 88 and guide shaft 90 maintain the spool cage 58 around the spool 46 as the actuator assembly 40 is transported horizontally across the inner side 92 of the gateway panel 26.

The inner side 92 of the gateway panel 26 has upper and lower pin racks 94 and 96 that are formed by U-channels 98 that accommodate the series of blocking pins 69 that project in pairs into each guide channel 28. The upper blocking pins 100 block the passage from the storage magazine 18 through the gateway panel 26 until the pin is retracted allowing a cap 16 to drop to the simultaneously extended lower blocking pin 102. When the lower blocking pin 102 is retracted, the tube cap 16 resting on the lower blocking pin 102 is released to a cap receptacle 104 on the cap carrier 42 positioned below the opened channel of the gateway panel 26.

Simultaneously, the upper pin 100 is extended preventing caps from the magazine 18 from passing through the gateway. For clarity, the upper pin 100 and the lower pin 102 are shown displaced from the actuator assembly 40, but each of the pins 69 in the series of upper and lower pins 100 and 102 is biased by a compression spring 105 to maintain controlled positioning during operation.

The cap carrier 42 is part of the overall displaceable actuator assembly 40. Together with the block and release mechanism 38, the cap carrier 42 is transported in a housing carriage 106 toward the orientation station 44. The housing carriage 106 has an attached guide block 107 that is slideably engaged with a rail 108 mounted along the inside back of the frame 14. The cap carrier 42 is slideably connected to the housing carriage 106 on guide rods 109 to extend the travel of the cap carrier 42 to the orientation station 44 outside the main frame 14 as shown in FIG. 1. Displacement of the housing carriage 106 and cap carrier 42 is accomplished by a drive belt 110 that loops around a drive capstan 111 and an idler wheel 112 on the intermediate deck 15.

Figure 7:
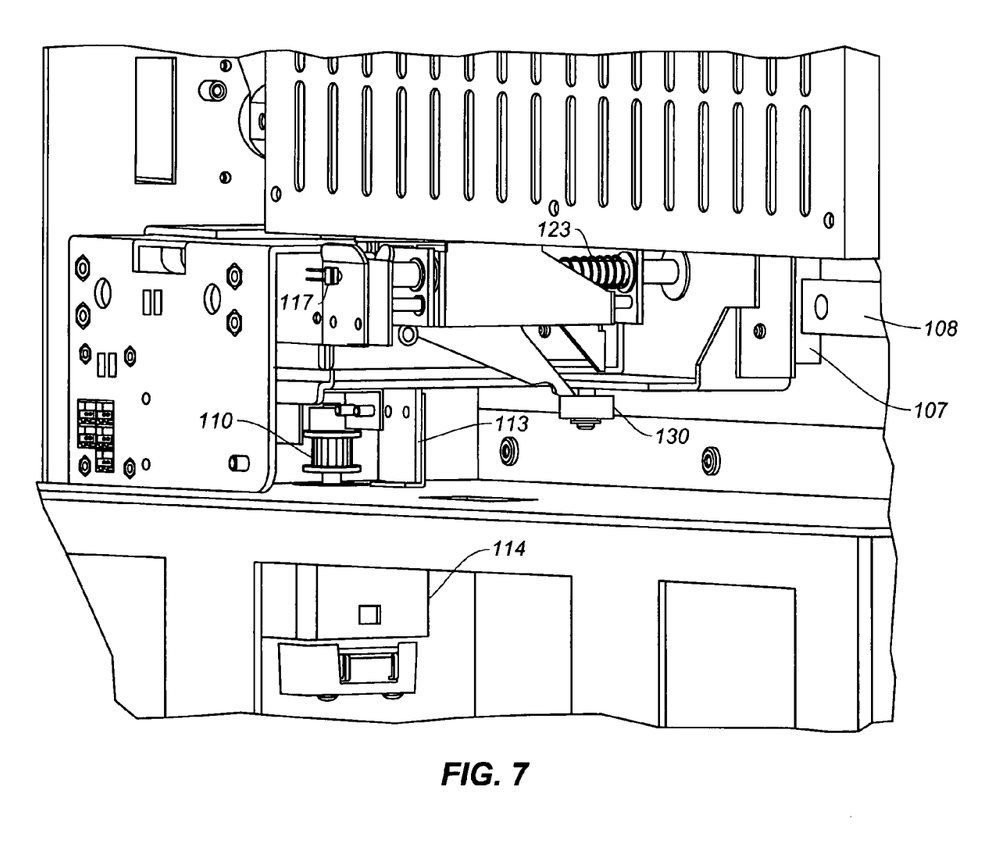

The drive belt 110 has a point of attachment to a tab 113 that depends from the cap carrier 42 as shown in the enlarged, partial perspective view of FIG. 7 with the drive belt removed for clarity. Rotation of a stepping motor 114 drives the drive capstan 111 and looped drive belt 112 and displaces the cap carrier 42 and connected housing carriage 106 alongside the gateway panel 26. When the cap carrier 42 has received a cap 16 and is programmed to travel the extended distance to the orientation station 44, the housing carriage 106 is halted in its travel by a stop (not visible) and the cap carrier 42 with its pivotally connected actuator assembly 40 advances to project a portion of the cap carrier 42 and the actuator assembly 40 outside of the internal frame 14 to the orientation station 44.

During operation the housing carriage 106 and the carried cap carrier 42 are transported to a selected position under one of the guide channels 28 of the gateway panel 26 where a tube cap 16 trapped in the guide channel 28 is released by the block and release mechanism to the receptacle 104 at the end of the cap carrier 42.

The cap carrier 42 of the actuator assembly 40 has a retractable presentation pin 116 in a pivotal housing 118. The presentation pin 116, which has been retracted by action of the block and release mechanism 38 is urged against the inside of the tube cap 16 that has been released to the receptacle 104 of cap carrier 42. In the event the presentation pin 116 is urged against the top of an incorrectly loaded cap or an empty receptacle 115, the anomaly is sensed by sensors 117, and the cap is ultimately rejected at the orientation station 44 or the sequence is aborted. A cap 16 that is correctly positioned is retained by the presentation pin 116 which is biased by a spring 123. The presentation pin 116 is a mounting post for positioning the tube cap 16 at a specified location for pickup.

As shown in FIG. 4, the block and release mechanism 38 has a depending tab 120 that engages a flange 122 on the internal end of the presentation pin 116. On rotation of the spool 46 of the block and release mechanism the presentation pin 116 is retracted while the tube cap 16 simultaneously seats in the receptacle 104 of the cap carrier 42. On reverse rotation of the spool 46, the pins 88 reverse allowing the next tube cap to drop into the ready position. The presentation pin 116 when released extends a contact end 119 (shown in dotted line) that contacts the inside of a tube cap 16 trapped in the receptacle 104.

The captured tube cap 16 retained by the extended presentation pin 116 is then shuttled to the orientation station 44 at one end of the internal frame 14. As the housing carriage 106 with the block and release mechanism 38 reaches the limit of its travel, a pivotal, depending latching roller 130, shown in FIG. 7, contacts a projecting ramp 131, to unlatch the cap carrier 42 and pin actuator housing 118 from the main housing carriage 106. The released cap carrier 42 continues independent travel on the guide rods 109 to the orientation station 44.

Figure 5:
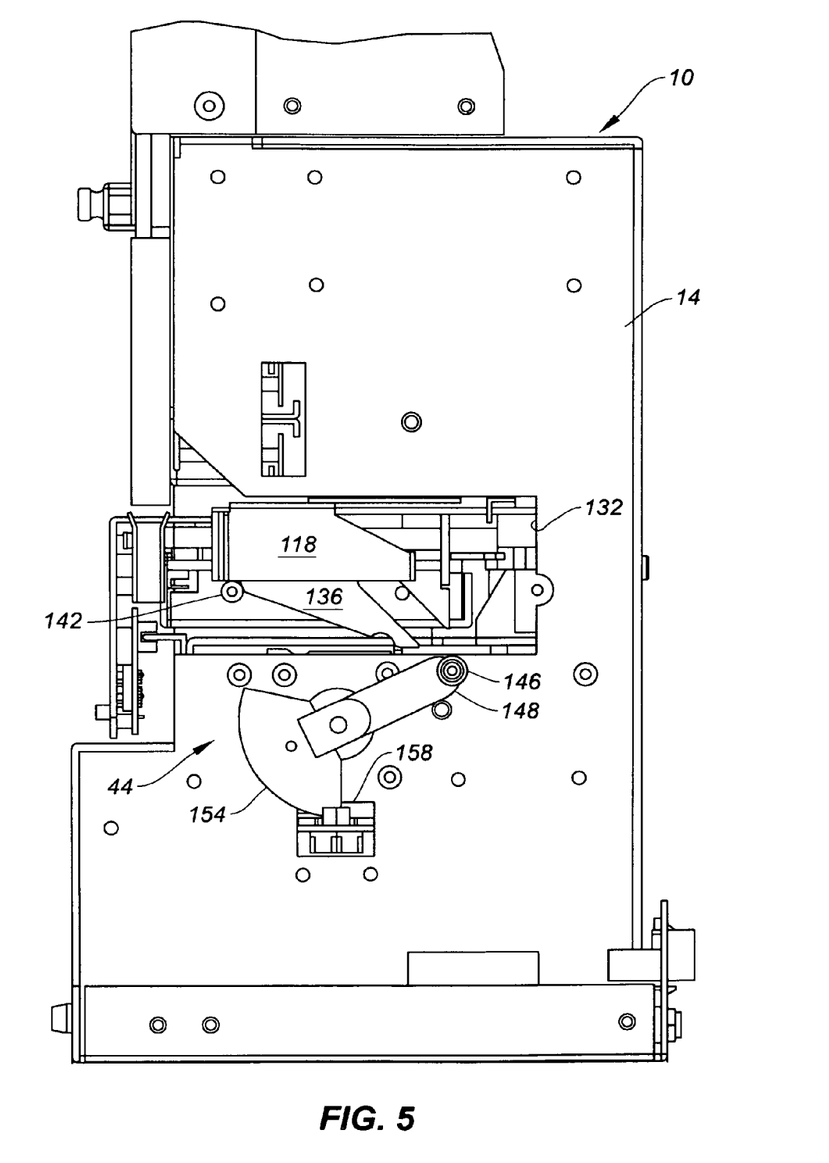
FIG. 5 is an end view of the tube cap presenter of FIG. 1 with the tube cap carrier located at an orientation station.
Figure 6:
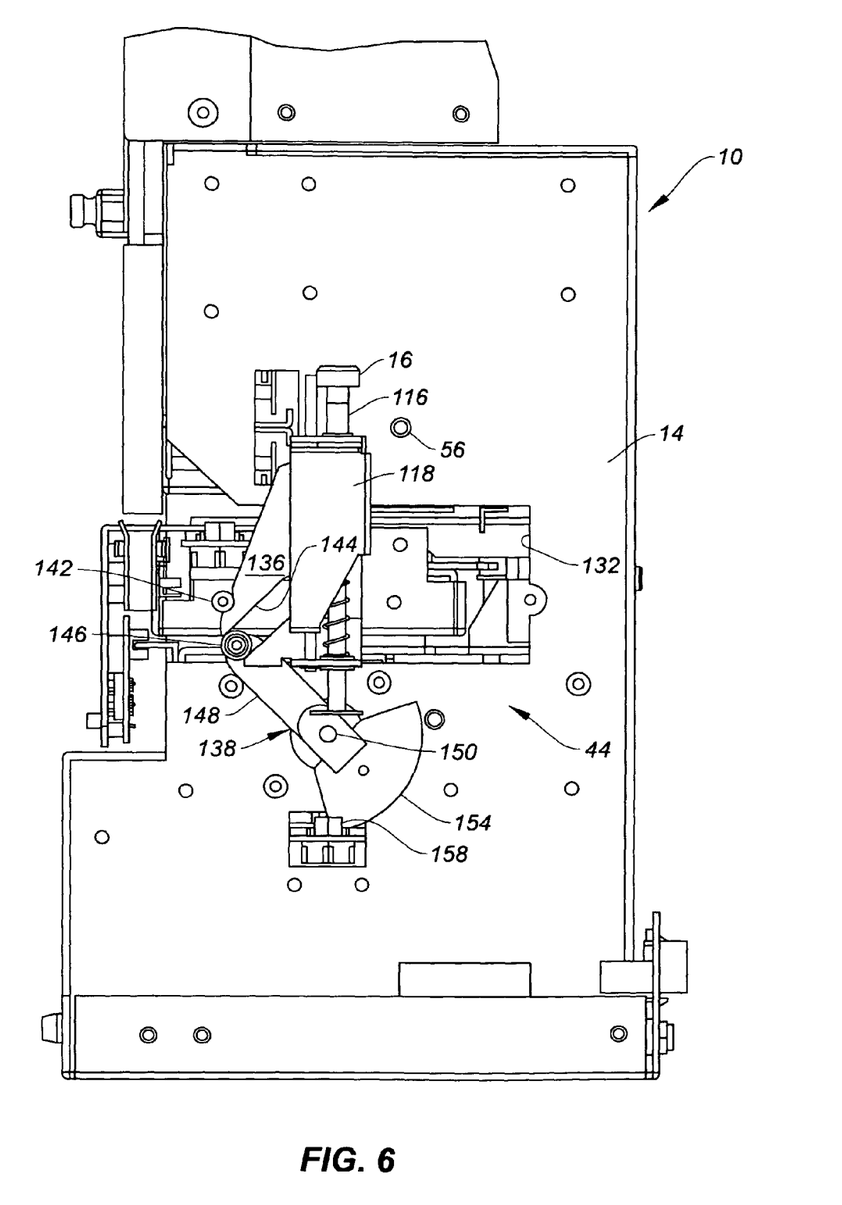
FIG. 6 is an end view of the tube cap presenter of FIG. 1 with the tube cap carrier located at the orientation station and a tube cap presentation pin raised to a presentation position.

A second stationary stabilizer pin 121 in the pivotal housing 118 of the actuator assembly 40 cooperates to hold a cap 16 on the contact end 119 of the presentation pin 116 as it travels to the orientation station 44, as shown in FIGS. 5 and 6. It is to be understood that certain of the cooperation actuating elements are shown displaced from one another for clarity, but are typically biased by springs that typically urge one element against the other as is well known in the art.

The pivotal housing 118 for the presentation pin 116 of the cap carrier 42 extends through an opening 132 in the internal frame 14, as shown in FIGS. 1, 5 and 6. The pivotal housing 118, as shown in FIG. 4, has a pivot axel 134 and a depending cam plate 136 that is engageable by a pivot actuator 138 on the outside of the frame 14 at the orientation station 44. The cam plate 136 of the pivotal housing 118 has a stop pin 142, and a cooperating cam slot 144 that is engageable with an actuator roller 146 on the end of a crank arm 148 of the pivot actuator 138. The crank arm 148 pivots on drive shaft 150 connected to a drive motor 152. The crank arm 148 has a diametric extension plate 154 that cooperates with a sensor unit 158 to sense rotational travel of the crank arm 148.

As shown in FIG. 5, the extended presentation pin 116 engages the inner side of the tube cap 16 positioned in the receptacle 104 of the cap carrier 42 located at the orientation station 44. While engaging the tube cap 16 the drive motor 152 is activated and the crank arm 148 swings the actuator roller 146 into engagement with the cam slot 144 of the cam plate 136. As the actuator roller 146 travels in the cam slot 144, the pivotal housing 118 with the presentation pin 116 swings a quarter turn with an upward lift until cam plate 136 is restricted by the stop pin 142 to a holding location, as shown in FIG. 6. In the position shown in FIG. 6, the presented cap 16 can be conveniently removed manually, or more typically, by an accessory robotic pickup mechanism of a capping machine.

Referring again to FIG. 1, the tube cap presenter 10 has an electronics compartment 162 below the intermediate deck 15 having one or more electronic circuit boards 164 that provide the electronics for controlling the operation. The circuit boards 164 include a controller with an internal processor 166 for the electromechanical operation of the system. The tube cap presenter 10 also includes an electronic interface to an external processor such as a general purpose computer or the control system of an auxiliary system such as an automated capper.

The sequence of operations can be controlled with a user application with a variety of options suitable to a particular task. For example, each of the vertical guide channels can be filled with caps of different color or barcode class marking and can be selectively accessed according to the requirement of the user. Or, for expediency, caps in the vertical guide channels closest to the presentation station can be first exhausted before moving to the next closest channel. These and other variations in operation are expected and do not depart from the scope of the claims.

The invention claimed is:

1. A laboratory tube cap presenter that selectively presents a tube cap for a laboratory tube from a tube cap supply to a tube cap pickup location comprising:
   a frame having an external housing;
   a storage magazine vertically mounted on the frame having at least one slot for containing a plurality of tube caps, wherein the slot is sized to contain tube caps in a uniform side to side orientation;
   a sorting shunt having an actuator assembly with a block and release mechanism that selectively releases a single tube cap and blocks remaining tube caps in the storage magazine on activation of the actuator assembly;
   a cap carrier that receives a tube cap released from the sorting shunt;
   a presentation pin that is contactable with a tube cap received by the cap carrier;
   an orientation station displaced from the storage magazine;
   a transport system connected to the cap carrier that transports a tube cap to the orientation station when a tube cap is received by the cap carrier; and
   a pivot actuator that pivots the presentation pin and a tube cap at the orientation station to a pickup position for tube cap pickup.

2. The laboratory tube cap presenter of claim 1 wherein the presentation pin is a support post that supports a tube cap at the orientation station on vertical positioning of the support post.

3. The laboratory tube cap presenter of claim 2 wherein the support post includes a stabilizer member to assist in retaining the tube cap on the support post.

4. The laboratory tube cap presenter of claim 1 wherein the storage magazine has a plurality of slots for containing multiple caps in each of the multiple slots.

5. The laboratory tube cap presenter of claim 4 wherein the plurality of tube caps in one slot is different than the plurality of tube caps in one of the other slots.

6. The laboratory tube cap presenter of claim 4 wherein the sorting shunt has a stationary gateway panel with guide channels that correspond to the slots in the storage magazine to selectively receive tube caps from the storage magazine.

7. The laboratory tube cap presenter of claim 6 wherein each guide channel of the gateway panel has a blocking device, wherein the actuator assembly has an actuator mechanism that cooperates with the blocking device to selectively release a tube cap to the cap carrier.

8. The laboratory tube cap presenter of claim 7 wherein the actuator mechanism of the actuator assembly is displaceable relative to the stationary gateway panel.

9. The laboratory tube cap presenter of claim 8 wherein the displaceable actuator mechanism is connected to the cap carrier and the transport system transports the actuator assembly and the connected cap carrier from guide channel to guide channel and the cap carrier to the orientation station.

10. The laboratory tube cap presenter of claim 7 wherein the actuator assembly includes a pair of upper and lower actuator elements.

11. The laboratory tube cap presenter of claim 10 wherein the blocking device of each guide channel has an upper and lower blocking pin selectively engageable with the upper and lower actuator elements of the actuator assembly wherein one tube cap from the magazine is blocked and simultaneously another tube cap is released when the actuator mechanism is actuated.

12. The laboratory tube cap presenter of claim 11 wherein the actuator assembly has an actuation spool connected to the upper and lower actuator elements and to a radial drive motor to simultaneously advance one actuator element and retract the other on part rotation of the drive motor.

13. The laboratory tube cap presenter of claim 12 wherein the presentation pin is connected to the actuator mechanism and engages a tube cap in the tube cap carrier on actuation of a blocking device of a selected guide channel of the gateway panel.

14. The laboratory tube cap presenter of claim 13 wherein the actuator mechanism and engaged tube cap in the tube cap carrier have a latch to enable transport of the actuator mechanism and engaged tube cap in the tube cap carrier to the orientation station separate from the actuation spool.

15. The laboratory tube cap presenter of claim 13 wherein the actuator mechanism and engaged tube cap in the tube cap carrier transported to the orientation station are engaged by the pivot actuator to pivot the presentation pin and engaged tube cap to a presentation position for pickup.

16. The laboratory tube cap presenter of claim 1 wherein the tube cap presenter further comprises:
   a controller that coordinates the operation of the tube cap presenter.

17. The laboratory tube cap presenter of claim 16, wherein the controller of the tube cap presenter is connected to a general purpose computer having a computer program that programs the protocol for use of the laboratory tube cap presenter.

18. The laboratory tube cap presenter of claim 1 in combination with a tube cap pickup mechanism.

* * * * *